United States Patent [19]

Walraevens et al.

[11] 4,424,391

[45] Jan. 3, 1984

[54] PROCESS FOR THE MANUFACTURE OF OLEFINE OXIDES

[75] Inventors: Rene Walraevens; Luc Lerot, both of Brussels, Belgium

[73] Assignee: Solvay & Cie, Brussels, Belgium

[21] Appl. No.: 420,320

[22] Filed: Sep. 20, 1982

Related U.S. Application Data

[63] Continuation of Ser. No. 147,624, May 7, 1980, abandoned.

[30] Foreign Application Priority Data

May 10, 1979 [FR] France ................................ 79 12145

[51] Int. Cl.$^3$ ......................................... C07D 301/14
[52] U.S. Cl. .................................. 549/525; 260/502 R
[58] Field of Search .......................................... 549/525

[56] References Cited

U.S. PATENT DOCUMENTS

| | | | |
|---|---|---|---|
| 2,877,266 | 3/1959 | Korach | 260/502 |
| 2,977,374 | 3/1961 | Phillips et al. | 549/525 |
| 4,113,747 | 9/1978 | Prescher et al. | 549/525 |
| 4,137,242 | 1/1979 | Prescher et al. | 549/525 |
| 4,172,840 | 10/1979 | Hildon et al. | 549/525 |
| 4,177,196 | 12/1979 | Hildon et al. | 549/525 |
| 4,193,929 | 3/1980 | Hildon et al. | 549/525 |
| 4,267,124 | 5/1981 | Hardy et al. | 260/502 R |

FOREIGN PATENT DOCUMENTS

| | | | |
|---|---|---|---|
| 554 | 2/1979 | European Pat. Off. | 549/525 |
| 555 | 2/1979 | European Pat. Off. | |
| 2747762 | 4/1978 | Fed. Rep. of Germany | |
| 1519147 | 2/1968 | France | |
| 2212331 | 7/1974 | France | |
| 2380268 | 9/1978 | France | |
| 846534 | 8/1960 | United Kingdom | 549/525 |

*Primary Examiner*—Norma S. Milestone
*Attorney, Agent, or Firm*—Spencer & Frank

[57] ABSTRACT

A process for the manufacture of olefine oxides, comprising reacting, with an olefine, an organic solution of percarboxylic acid which is obtained by reacting the corresponding carboxylic acid with hydrogen peroxide. The organic solvent employed is a mixture of inert organic solvents which does not form an azeotrope with the olefine to be epoxidized or with the olefine oxide, and which contains a volatile solvent, the boiling point of which is lower than that of the olefine oxide, and a solvent of low volatility, the boiling point of which is higher than that of the olefine oxide.

20 Claims, 3 Drawing Figures

PROCESS FOR THE MANUFACTURE OF OLEFINE OXIDES

CROSS REFERENCE TO RELATED APPLICATION

This application is a continuation application of applicants' copending United States Application Ser. No. 06/147,624 filed on May 7, 1980, now abandoned.

BACKGROUND OF THE INVENTION

The present invention relates to a process for the manufacture of olefine oxides by epoxidising the corresponding olefines with percarboxylic acids.

The manufacture of olefine oxides by reacting the corresponding olefines with percarboxylic acids, in the presence of organic solvents, is well known. Thus, for this purpose, French Patent Application 76/03,020, filed on Feb. 2, 1976 in the name of INTEROX CHEMICALS LTD., proposed the use of a solution of a percarboxylic acid in an inert organic solvent, the solution being obtained by reacting hydrogen peroxide with the corresponding carboxylic acid, in a two-phase medium and in the presence of a catalyst, such as sulphuric acid. The hydrogen peroxide is employed in the form of an aqueous solution and the carboxylic acid is employed in the form of a solution in the inert organic solvent. The two solutions circulate in countercurrent. However, although this process is much more advantageous than the other known processes, it still exhibits various disadvantages.

Thus, the resulting organic solution of peracid contains water and small amounts of sulphuric acid. These impurities are very troublesome in the subsequent epoxidation because they favour the rupture of the epoxide bridge and the formation of undesirable heavy by-products. Therefore, it is necessary to subject the organic solution of peracid to specific treatments for the purpose of removing these impurities therefrom.

Furthermore, the aqueous solution collected, which has a reduced content of hydrogen peroxide and contains dilute sulphuric acid, must be concentrated in order to be able to recover the unconverted hydrogen peroxide and the sulphuric acid and to recycle them. This concentration process is very difficult to carry out in view of the very high aggressivity of the above-mentioned products.

Moreover, the resulting solutions of peracids, which are intended to for employment in the epoxidation, are relatively dilute. Now, it is advantageous to use concentrated solutions of percarboxylic acid, for the epoxidation, in order to increase the epoxidation rate.

Finally, the reaction mixture obtained on epoxidation must be subjected to a large number of separations in order to recover each of its constituents separately.

SUMMARY OF THE INVENTION

The aim of the present invention is to provide a process which no longer exhibits the abovementioned disadvantages of the known processes. In particular, the process according to the invention makes it possible easily to remove the water formed during the manufacture of the peracid, to reduce the relative amounts of inert solvent employed and to reduce the undesirable secondary reactions during the epoxidation. Furthermore, it results in an increase in the reaction rate during the epoxidation. Moreover, it makes it possible to simplify the separation, by distillation, of the constituents of the reaction mixture resulting from the epoxidation, and to avoid secondary reactions in the boilers of the distillation columns. It further makes it possible to work under good safety conditions because the total concentration of peroxide compounds in each of the steps of the process is not high. Moreover, it facilitates the separation of the organic and aqueous phases during the manufacture of the peracid, because their extraction capacity is improved. Finally, it makes it possible to reduce the losses of reactants, in particular hydrogen peroxide, to a minimum.

For this purpose, the invention relates to a process for the manufacture of olefine oxides by epoxidising the corresponding olefines with an organic solution of a percarboxylic acid in an inert organic solvent, the percarboxylic acid being obtained by reacting the corresponding carboxylic acid with hydrogen peroxide, in the presence of a catalyst and the inert organic solvent. In this process, the inert organic solvent employed is a mixture of solvents which does not form an azeotrope with the olefine to be epoxidised or with the olefine oxide, and which comprises a volatile solvent, the boiling point of which is lower than the boiling point of the olefine oxide, and a solvent of low volatility, the boiling point of which is higher than the boiling point of the olefine oxide.

DETAILED DESCRIPTION OF THE INVENTION

Figure 1:
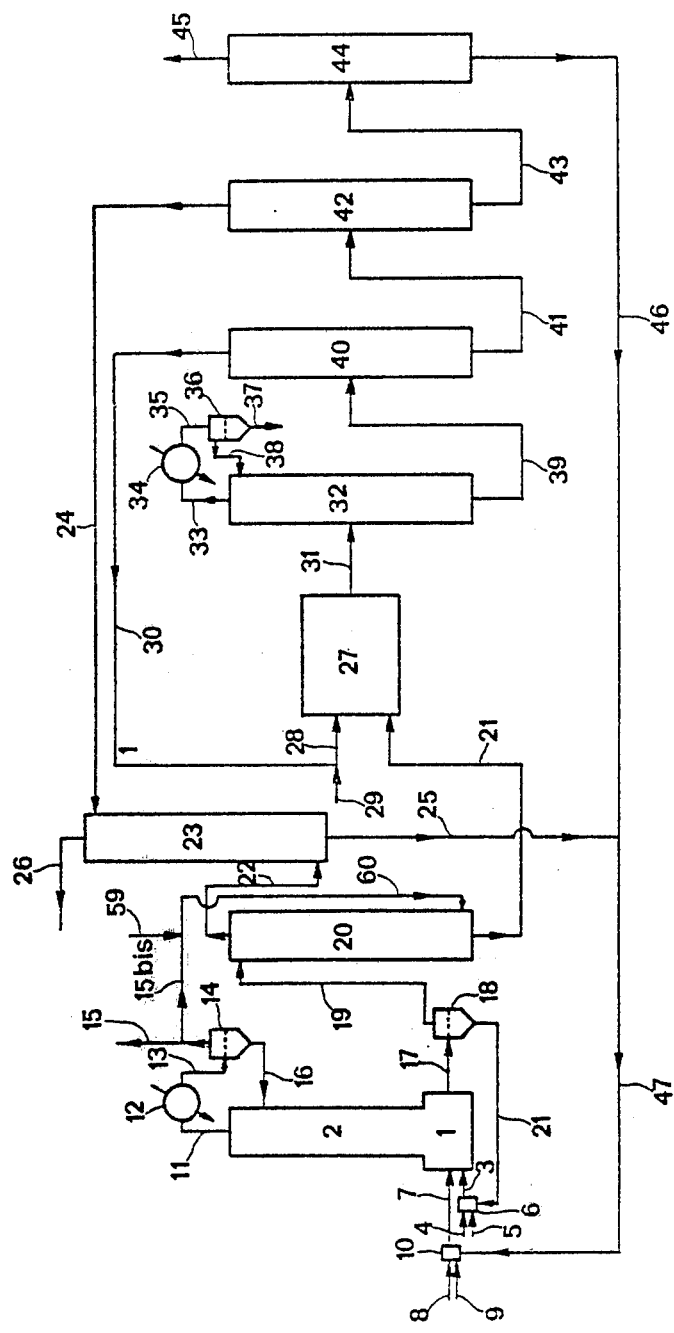
FIGS. 1, 2 and 3 are schematic diagrams of apparatuses for carrying out the process of the present invention in a continuous manner.

The organic solution of percarboxylic acid can be obtained by various methods which are in themselves known.

According to a preferred embodiment of the process according to the invention, the organic solution is manufactured by continuously reacting the corresponding carboxylic acid with hydrogen peroxide, in the presence of a catlyst and an inert organic solvent. The volatile solvent is chosen from among those which are capable of forming a heterogeneous azeotrope with water, so that the water present in the reaction mixture can be removed by distillation of the water/volatile solvent azeotrope. However, a sufficient amount of water is kept in the reaction mixture to allow the formation of an aqueous phase which is distinct from an organic phase containing the inert organic solvent and the percarboxylic acid. The aqueous phase is separated from the organic phase, which constitutes the organic solution of percarboxylic acid, by decantation.

The inert organic solvent employed, which contains the volatile solvent and the solvent of low volatility, must be inert towards the constituents of the reaction mixture during the manufacture of the percarboxylic acid, under the conditions of this manufacture, and towards the constituents of the reaction mixture from the epoxidation, under the conditions of the epoxidation.

Moreover, the inert organic solvent must dissolve the percarboxylic acid as the latter is formed during its manufacture. Preferably, the constituents of the inert organic solvent are chosen so that, under the reaction conditions, the solubility of the peracid in the organic solution is equal to at least 0.05, expressed in mols per liter.

Furthermore, the constituents of the inert organic solvent are chosen from among those which do not form an azeotrope with the olefine to be epoxidised or with the olefine oxide.

Finally, it is advantageous to employ an inert organic solvent which is very sparingly soluble in water and in which water is very sparingly soluble. Preferably, the inert organic solvent is chosen such that the water content of the organic solution of peracid, during its manufacture, is less than the water content of the water/volatile solvent azeotrope under the same temperature and pressure conditions. Most frequently, the inert organic solvent is chosen such that the amount of water in the organic solution of peracid is less than 5% and preferably less than 1% by weight. On the other hand the choice of the total amount of inert organic solvent dissolved in the aqueous phase is less important. In general, care is taken to choose an inert organic solvent which is such that this total amount does not exceed 10% and most frequently 5% by weight. Moreover, the inert organic solvent chosen is such that the densities of the aqueous and organic phases obtained during the manufacture of the peracid are sufficiently different to enable them to be separated by decantation.

The volatile solvent present in the inert organic solvent generally satisfies a certain number of characteristics. It is capable of forming, with water, a heterogeneous azeotrope with a minimum boiling point which, under equivalent pressure conditions, must be lower than the boiling point of the other constituents and of the other possible azeotropes which could be formed in the reaction mixture from the manufacture of the peracid. It does not form an azeotrope with the carboxylic acid. Its boiling point under atmospheric pressure does not generally exceed 390 K. In fact, solvents having a higher boiling point do not make it possible, in practice, to remove the water azeotropically when manufacturing the peracid. In general, solvents having a boiling point which is not lower than 330 K are employed. Solvents having a lower boiling point are suitable but are less advantageous from an economic point of view because they must be employed in much greater amounts. Most frequently, volatile solvents having a boiling point of between 333 and 383 K, under atmospheric pressure, are used. Good results have been obtained by employing volatile solvents having a boiling point of between 340 and 375 K under atmospheric pressure.

The organic solvent of low volatility, present in the inert organic solvent, also generally satisfies a certain number of characteristics. Its boiling point is higher than that of the olefine and of the olefine oxide, under equivalent pressure conditions. In the case where it is capable of forming an azeotrope with the carboxylic acid, the boiling point of this azeotrope is higher than those of the olefine and the olefine oxide.

If appropriate, the inert organic solvent can contain several volatile organic solvents and several organic solvents of low volatility.

All organic compounds which are liquid under the reaction conditions and satisfy the conditions defined above can be suitable as solvents for carrying out the process according to the invention. These liquid compounds are generally chosen from among carboxylic acid esters, ethers, halogenohydrocarbons, unsubstituted hydrocarbons and hydrocarbons substituted by nitro groups, nitric acid esters and non-acidic esters of carbonic and phosphoric acids, which satisfy the conditions defined above.

Appropriate solvents can thus be chosen from among the aliphatic, alicyclic or aromatic esters of monocarboxylic or polycarboxylic acids with monohydric or polyhydric alcohols, containing from 4 to 20, and preferably from 4 to 10, carbon atoms in the molecule.

Among these esters, the following are particularly suitable: isopropyl, propyl, butyl, isobutyl, sec.-butyl, tert.-butyl, amyl, isoamyl and sec.-amyl formates and acetates, methyl, ethyl, propyl, isopropyl, butyl, isobutyl and isoamyl monochloroacetates and dichloroacetates, propionates, butyrates and isobutyrates, methyl, ethyl and propyl valerates, isovalerates and carproates, methoxyethyl, ethoxyethyl and cyclohexyl acetates, methyl pivalate and the diethyl esters of phthalic and adipic acids.

The following may be mentioned as ethers which are generally suitable: symmetric or asymmetric aliphatic ethers containing from 4 to 12 carbon atoms, such as 2,2'-dichlorodiethyl ether, butyl ethyl ether, tert.-butyl ethyl ether, tert.-amyl methyl ether, diisopropyl ether, dipropyl ether, dibutyl ether, ethyl hexyl ether and diisobutyl ether.

The following may be mentioned as halogenohydrocarbons which are generally suitable: aromatic, aliphatic and alicyclic halogenohydrocarbons which contain from 1 to 8 carbon atoms in their molecule and are substituted by at least one halogen preferaly chosen from amongst chlorine, fluorine and bromine. Particularly suitable halogenohydrocarbons are carbon tetrachloride, chloroform, methylene chloride, di-, tri-, tetra- and penta-chloroethanes, trichlorotrifluoroethanes, tri- and tetra-chloroethylene, mono-, di- and tri-chloropropanes, monochloro- or polychloro-butanes, -methylpropanes, -pentanes and -hexanes, mono- and di-chlorobenzenes and chlorotoluenes.

The following may be mentioned as hydrocarbons substituted by nitro groups, which are generally suitable: aromatic, aliphatic or alicyclic hydrocarbons containing from 3 to 8 carbon atoms, such as nitropropanes, nitrobenzene and nitrocyclohexane.

The following may be mentioned as unsubstituted hydrocarbons which are generally suitable: aliphatic, aromatic or alicyclic hydrocarbons containing from 5 to 14 carbon atoms, such as benzene, toluene, xylene, pentane, hexane, heptane, octane, diisobutyl(2,5 dimethylhexane), cyclohexane, methylcyclohexane and tetralin.

The following may be mentioned as carbonic acid esters which are generally suitable: aliphatic esters containing from 3 to 9 carbon atoms in the molecule, such as dimethyl, diethyl, diisobutyl, dibutyl, di-tert.-butyl, dipropyl and diisopropyl carbonates. Nitric acid esters containing from 1 to 5 carbon atoms in the molecule, such as methyl, propyl, butyl and isoamyl nitrates, are suitable. As regards suitable phosphoric acid esters, they are those which correspond to the formula:

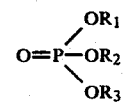

in which $R_1$, $R_2$ and $R_3$ are identical or different and represent alkyl, aryl, arylalkyl or alkylaryl groups which are such that the molecule contains from 3 to 30 carbon atoms. Particular examples of phosphates which may be mentioned are trimethyl, tributyl, trioctyl and dioctyl phenyl phosphates.

Among the suitable solvents, the volatile solvents which are advantageously chosen are solvents such as 1,1-dichloropropane, 1,2-dichloropropane, cyclohexane, 1,2-dichloroethane, carbon tetrachloride, toluene and benzene. Good results have been obtained with 1,2-dichloropropane and 1,2-dichloroethane.

The solvents of low volatility which can advantageously be chosen are solvents such as 1,2,3-trichloropropane, tetrachloroethanes, tetrachloroethylene, pentachloroethane, 1,4-dichlorobutane, meta-xylene, para-chlorotoluene, chlorobenzene, 1-nitropropane, nitrobenzene, methyl and ethyl chloroacetates, butyl acetate, diethyl carbonate and tributyl phosphate. Good results have been obtained with 1,2,3-trichloropropane and 1,1,2,2-tetrachloroethane in the case where the boiling point of the olefine oxide is lower than 415 K. 1,1,2,2-Tetrachloroethane has proved particularly appropriate.

Very good results have been obtained from the epoxidation of allyl chloride to give epichlorohydrin, by using a mixture of 1,1,2,2-tetrachloroethane and 1,2-dichloropropne as the inert organic solvent.

The relative amount of volatile solvent and of solvent of low volatility can vary within wide limits. In general, the inert organic solvent used contains from 5 to 60% by weight of volatile solvent. Preferably, the proportion by weight of volatile solvent used is less than that of the solvet of low volatility. Good results have been obtained by using a mixture containing from 5 to 35% by weight of volatile solvent.

Accordng to an embodiment of the process according to the invention, part of the reaction mixture for the manufacture of the peracid is removed continuously, the aqueous phase and the organic phase, in the removed part, are separated by decantation, and the aqueous phase, separated off in this way, is reintroduced into the reaction mixture. If appropriate, after the organic phase has been subjected to complementary treatments involving coalescence and decantation, it can be sent to the epoxidation reaction. Preferably, the organic phase, which constitutes the organic solution of peracid and which can contain small amounts of hydrogen peroxide, is washed with water before being sent to the epoxidation reaction, so as to remove the unconverted hydrogen peroxide therefrom. To do this, it is possible to use fresh water or also, advantageously, the water collected after condensation and separation, by decantation, of the heterogeneous water/volatile organic solvent azeotrope removed by distillation during the peracidification, or mixtures of the latter. The water is generally employed at a rate of 0.01 to 100%, and preferably 0.1 to 20%, of the weight of the organic phase to be washed. This washing can be carried out at variable temperatures. In general, it is carried out at temperatures between 263 and 323 K and preferably between 268 and 300 K. A purified organic solution containing the carboxylic peracid which is used for the epoxidation of the olefine, and an aqueous solution containing hydrogen peroxide and, if appropriate, catalyst, are thus obtained.

According to another preferred, embodiment of this invention the aqueous solution containing hydrogen peroxide is washed with at least part of the volatile organic solvent collected during the separation, by distillation, of the reaction mixture from epoxidation, in order to extract the hydrogen peroxide therefrom. The amount of volatile solvent employed for carrying out this second washing can vary substantially. In general, the volatile solvent is employd at a rate of 0.1 to 20 times, and preferably from 0.2 to 10 times, the weight of aqueous solution to be treated. This second washing can be carried out at variable temperatures. In general, it is carried out at temperatures between 273 and 373 K and preferably between 280 and 323 K.

The resulting solution of hydrogen peroxide in the volatile organic solvent is sent to the manufacture of the peracid.

As regards the aqueous solution exhausted of hydrogen peroxide, it can be subjected to various treatments for the purpose of recovering the small amounts of volatile solvent which could be dissolved therein. It is thus possible to carry out steam distillation, to condense the resulting gas phase and to subject the resulting liquid to decantation in order to collect the volatile organic solvent, which is recycled to the manufacture of the peracid.

The volatile organic solvent, possibly containing hydrogen peroxide, can be pre-mixed with the organic solution of carboxylic acid in the organic solvent of low volatility, the said organic solution being collected on distillation of the mixture from epoxidation. These two solutions can also be introduced separately into the reactor for the manufacture of the peracid.

The process according to the invention is particularly suitable for the manufacture of olefine oxides having a boiling point of at least 370 K under atmospheric pressure. It can thus be applied to the epoxidation of a large number of different olefines containing at least one carbon-carbon double bond. The process is preferably applied to olefines which contain $>C=CH_2$, $—CH=CH—$ or $—CH=CH_2$ groups. In general, the process is applied to alkenes or cycloalkenes containing from 3 to 30 carbon atoms and is most frequently applied to those containing a total of 3 to 10 carbon atoms in their molecule.

The alkenes or cycloalkenes to which the process can be applied can be unsubstituted or substituted by one or more substituents chosen from among alkyl groups generally containing from 1 to 4 carbon atoms, cycloalkyl groups and aryl grouups, or substituents containing hetero-atoms. Among the alkenes or cycloalkenes which are unsubstituted or substituted solely by alkyl, cycloalkyl or aryl groups, and to which the process according to the invention is applied, the following may be mentioned more particularly: butadiene, pentadienes, in particular isoprene, hexenes, hexadienes, diisobutylene, octenes, decenes, α-pinene, p-menthene, styrene, methylstyrene, vinyl toluene, vinyl cyclohexane and vinyl cyclohexene, cyclohexene, divinyl benzene and stilbenes.

The alkenes or cycloalkenes which can be used in the process of the invention can also be substituted by one or more substituents containing hetero-atoms, such as halogen atoms, more particularly chlorine, fluorine and bromine atoms, sulphonic acid or phosphoric acid groups and hydroxyl, alkoxy, carboxyl, acyl, alkoxycarbonyl, aryloxycarbonyl, acyloxy, cylamino, arylamido, alkylamido, imido or nitrilo groups.

Allyl and methallyl chlorides and bromides may be more particularly mentioned as unsaturated halogen derivatives which can be used. Allyl alcohol, methallyl alcohol and methyl vinyl carbinol may be more particularly mentioned among the unsaturated alcohols which can be used. Methyl allyl ether, ethyl allyl ether and acrolein acetals may be mentioned as suitable unsaturated ethers. Suitable unsaturated esters include esters of unsaturated acids, such as acrylic, methacrylic and maleic acids, with saturated or unsaturated alcohols, and also esters of saturated acids with unsaturated alcohols, such as allyl alcohol and methallyl alcohol. The process of the invention can be applied in particular to methyl acrylate, ethyl methacrylate, diethyl maleate, allyl acetate, methallyl acetate and allyl propionate. Unsaturated ketones and aldehydes can also be used in the process of the invention, although, in the latter case, competitive reactions involving oxidation of the aldehyde group can appear. Methyl vinyl ketone, methyl allyl ketone and acrolein should be mentioned as ketones or aldehydes which can be used. Allylacetamide is included among the unsaturated amides to which the process according to the invention can be applied. Further examples of olefines to which the process of the invention can be applied are described in U.S. Pat. No. 2,977,374, filed on Mar. 7, 1958 and granted to UNION CARBIDE CORPORATION.

The process according to the invention is applied with particular success to the epoxidation of cyclohexene, butadiene, allyl alcohol, styrene and, very particularly, allyl chloride.

Various types of carboxylic acids can be used for the manufacture of the peracid employed for the epoxidation of olefines in the process according to the invention. In general, the carboxylic acid employed has a higher boiling point than the olefine oxide, under the same pressure conditions. These carboxylic acids can be monocarboxylic or polycarboxylic aids. In the latter case, the polycarboxylic acid can also be employed in the form of the corresponding anhydride in the process according to the invention. In general, carboxylic acids containing from 1 to 10 carbon atoms are employed, such as aliphatic, alicyclic or aromatic carboxylic acids which include, for example formic acid, acetic acid, chloroacetic acids, propionic acid, butanoic acid, maleic acid or anhydride, benzoic acid, cyclohexanecarboxylic acid and phthalic acids and anhydride. In the manufacture of epichlorohydrin, particularly advantageous results have been obtained by employing propionic acid.

The solutions of carboxylic acid in the inert organic solvent which are employed in the manufacture of the percarboxylic acid generally contain from 2 to 60%, and preferably from 5 to 60%, by weight of carboxylic acid. To prepare these solutions, it is advantageous to use the solution of carboxylic acid in the solvent of low volatility, which solution is recovered during the distillation of the reaction mixture from epoxidation, and the volatile solvent which is independently recovered during the same distillation steps, particularly after it has been used for recovering the hydrogen peroxide which was not converted in the manufacture of the peracid, in accordance with the variants described above. It is also possible to use the volatile solvent originating from the separation of the distilled azeotrope by decantation, and fresh solvents.

The hydrogen peroxide used for the reaction can be employed either in the pure state or in the form of aqueous solutions. If the hydrogen peroxide is employed in the form of an aqueous solution, it is advantageous to use concentration hydrogen peroxide solutions containing from 20 to 90% by weight of hydrogen peroxide. Other concentrations are also suitable but are less favourable. In fact, at the lowest concentrations of hydrogen peroxide, the amounts of water to be removed by azeotropic distillation are very large, while more highly concentrated hydrogen peroxide solutions are difficult to produce industrially.

In the reaction mixture for the manufacture of the peracid, the proportions of reactants can vary within wide limits, in absolute terms and relative to one another, depending, in particular, on the chosen rates of introduction of the reactants. Thus, the amount of hydrogen peroxide is generally between 0.1 and 10, and preferably between 0.2 and 5, mols per mol of carboxylic acid group. The most advantageous results are usually obtained when the amounts of hydrogen peroxide and carboxylic acid introduced into the reaction mixture are in a ratio which is close to or slightly less than the stoichiometric ratio. Thus, the hydrogen peroxide and the carboxylic acid are preferably introduced in amounts which are such that between 0.1 and 2, and preferably between 0.3 and 1.2, mols of hydrogen peroxide are introduced per mol of carboxylic acid group.

The hydrogen peroxide can be introduced directly into the reactor or into the aqueous solution of catalyst which is sent to the reactor, in the case where the catalyst is soluble in water. Thus, it is possible to introduce the hydrogen peroxide into the aqueous phase which is collected by separation of the reaction mixture by decantation and is continuously recycled to the reactor. This introduction is advantageously carried out in stages so as to avoid excessively high local concentrations of hydrogen peroxide. The rate at which the aqeous phase is continuously recycled must be sufficient for the composition of the resulting aqueous phase enriched in hydrogen peroxide to be always such that the reaction mixture remains outside the explosibility limits. Advantageously, the hydrogen peroxide can also be introduced directly into the reactor.

The catalyst employed is generally an acid catalyst suitable for esterification reactions, such as, for example, sulphuric acid, alkyl-, aryl-, arylalkyl- and alkylaryl-sulphonic acids, phosphoric acid, alkyl, aryl, alkylaryl and arylalkyl acid phosphates, trifluoroacetic acid, acetylsulphoacetic acid and also ion exchange resins of the sulphonated polymer or copolymer type. Preferred catalysts which may be more particularly mentioned are sulphuric acid and methane-, ethane-, benzene-, toluene-, xylene-, butane-, propane- and naphthalene-sulphonic acids. Among these catalysts, it is preferred to use those which are soluble in water and are insoluble or sparingly soluble in the organic liquid. The best results are obtained with the water-soluble catalysts of which the concentration in the organic phase is less than 3% and preferably less than 1% by weight, under the reaction conditions. Particularly advantageous results have been obtained with sulphuric acid.

The concentration of catalyst in the reaction mixture can vary within wide limits. To obtain high reaction rates, high concentrations of catalysts are generally used. In general, the amount of catalyst used is more than 5% of the total weight of carboxylic acid and percarboxylic acid which are present in the reaction mixture. The content of catalyst by weight is preferably between 0.1 and 30 times the total weight of carboxylic acid and percarboxylic acid which are present in the reaction mixture. The best results are obtained when this content is between 0.2 and 10 times the total weight of carboxylic acid and percarboxylic acid.

The catalyst can be employed in the pure state. However, if it is soluble in water, it is advantageously employed in the form of an aqueous solution. In this case, the catalyst can advantageously be employed by reintroducing, into the reaction mixture, the aqueous phase originating from the separation of the latter by decantation, if necessary after having replenished this aqueous phase with catalyst. In general, the concentration of water-soluble catalyst in the aqueous phase is between 10 and 60% by weight.

In general, a sufficient amount of water is kept in the reaction mixture so that the weight ratio of the aqueous phase to the organic phase, in the reaction mixture, is more than 0.05. Preferably, this ratio is more than 0.1. The best results are obtained when this ratio is more than 0.2.

Furthermore, in the majority of cases, no advantage is gained by keeping, in the reaction mixture, amount of water which are such that the weight ratio of the aqueous phase to the organic phase is more than 20. Preferably, this ratio is less than 10. The best results are obtained when it is less than 5.

The aqueous phase generally comprises from 5 to 95%, and most frequently from 10 to 70%, of its weight of water, the remainder substantially being formed by the constituents of the reaction mixture and mainly by the hydrogen peroxide and the catalyst, in the case where the latter is soluble and not in the form of a solid suspension. In general, the aqueous phase also comprises part of the carboxylic acid and part of the percarboxylic acid.

The water present in the aqueous phase can originate, in particular, from the reaction or from the introduction of certain constituents of the reaction mixture, in general the hydrogen peroxide and possibly the catalyst, in the form of aqueous solutions. In can also have been added intentionally.

The organic phase, which constitutes the organic solution of peracid, generally comprises from 30 to 98%, and most frequently from 40 to 95%, of its weight of inert organic solvent, the remainder being substantially formed by constituents of the reaction mixture and mainly by the carboxylic acid and the percarboxylic acid.

The organic phase can also contain small amounts of hydrogen peroxide and possible small amounts of catalyst. In general, the hydrogen peroxide content of the organic phase does not exceed 5% of its weight and its catalyst content does not exceed 1% of its weight. Most frequently, the hydrogen peroxide content and catalyst content of the organic phase do not exceed 2 and 0.4% of its weight, respectively.

The temperature of the reaction mixture is generally chosen below 373 K and is most frequently between 293 and 343 K. Higher temperatures are less advantageous because they involve a risk of violent decomposition of the peroxide compounds. The pressure is adjusted as a function of the temperature so as to maintain boiling. It can thus vary within wide limits. It is most frequently between 1 E+03 Pa and 1.2 E+05 Pa.

The heat required to maintain boiling can be supplied in accordance with conventional techniques which are in themselves known. Thus, the reaction mixture (aqueous phase and organic phase) can be heated by bringing it into contact with an exchange surface heated by means of a heat-transfer fluid, such as steam. Advantageously, it is also possible to introduce, into the reaction mixture, one or more of the constituents of the reaction mixture in vapour form. It is advantageous to introduce, in vapour form, the volatile organic solvent originating from the condensation and separation, by decantation, of the water/volatile solvent azeotrope, the volatile solvent originating from the distillation of the reaction mixture from epoxidation, if appropriate after it has been used for recovering the hydrogen peroxide from the organic phase removed from the reactor for the manufacture of the peracid, or mixtures thereof.

To carry out the manufacture of the peracid in accordance with the preferred embodiment, it is possible to use any equipment which is suitable for liquid reaction mixtures, in particular vat reactors fitted with a stirring system. More particularly, it is advantageous to use reactors which make it possible to distil one of the constituents of a liquid reaction mixture during the reaction, such reactors being in themselves known. In general, the process is carried out using reactors which make it possible to ensure intimate mixing of the aqueous and organic phases and good exchange between the liquid phases and the gas phase so as to assist the vaporisation of the water/organic liquid azeotrope.

These reactors are advantageously coupled to distillation columns, which are in themselves known, such as plate columns or stack columns.

The various parts of the reactors and columns in contact with the reaction mixture are advantageously made of corrosion-resistant materials, such as stainless steels, INCONEL, HASTELLOY, INCOLOY, NIMONIC, NI-RESIST and CHLORIMET alloys and enamelled steels.

The separation, by decantation, of the reaction mixture withdrawn from the reactor and that of the water-/organic liquid azeotrope collected at the top of the column can be carried out in accordance with various techniques which are in themselves known, such as settling by gravity or by the action of a centrifugal force, or passage through porous membranes selectively wetted by one or the other phase. Various types of apparatuses which are in themselves known can be used for this purpose. Thus, it is possible to use Florentine settling tanks, centrifugal settling tanks, separating filters with membranes, or electrical separators. The separation by decantation can be facilitated by an operation involving coalescence of the droplets in apparatuses which are in themselves known, such as mats or cartridges made of fibrous materials which are preferably wettable by the disperse phase.

The washing of the organic solution originating from the separation, by decantation, of the reaction mixture for the manufacture of the peracid, and the washing of the aqueous solution containing hydrogen peroxide, which results therefrom, can be carried out in various types of apparatuses which permit extraction and settling, such apparatuses being in themselves known. Thus, it is possible to use liquid/liquid extraction columns operating in countercurrent or settling mixers. The settling tanks can be of the type mentioned above.

As regards the actual epoxidation, it is general to use molar ratios of the percarboxylic acid to the olefine to be epoxidised of between 0.01 and 20. The molar ratio is preferably between 0.05 and 10. Small amounts of various additives, such as polymerisation inhibitors, stabilisers for the peracid, or sequestering agents, can also be added to the reaction mixture.

The epoxidation reaction is generally carried out at temperatures between 273 K and 423 K. These temperatures are preferably between 288 and 413 K. The reaction pressure is generally sufficient to maintain a liquid phase. It is generally between 1 E+03 Pa and 1 E+06 Pa. Of course, the reaction temperature and pressure depend on the particular nature of the olefine to be epoxidised.

To epoxidise allyl chloride and allyl alcohol, a temperature of 293 to 423 K and a pressure of 1 E+04 Pa and 1 E+06 Pa are most frequently used. The reactors used to carry out the epoxidation reaction are generally reactors which assist heat exchange so as to provide better control over the reaction temperatures. Thus, it is possible to use tubular reactors or autoclaves, a single reactor or reactors in cascades.

The reaction mixture obtained on epoxidation essentially consists of olefine oxide, carboxylic acid, solvent of low volatility, volatile solvent and unconverted reactants; it may contain small amounts of by-products and small amounts of various additives. Usually, it is subjected to preliminary separations so as to recover respectively, on the one hand, the unconverted olefine and the volatile organic solvent, and, on the other hand, a solution of olefine oxide in the organic solvent of low volatility, which solution can contain unconverted percarboxylic acid.

The olefine collected is advantageously recycled to the epoxidation reaction. To do this, the olefine can be absorbed in gaseous form in the organic phase containing the peracid, before sending it to the expoxidation. It is also possible to condense the olefine and then to send it by itself to the epoxidation. It is also possible to send the olefine directly in gas form into the epoxidation reactor so as to ensure the supply of at least part of the heat necessary to maintain the reaction temperature.

The liquid organic solution of olefine oxide and of carboxylic acid in the organic solvent of low volatility is then subjected to a separation, advantageously by distillation, so as to recover, on the one hand, the desired olefine oxide, and, on the other hand, the solution of carboxylic acid in the organic solvent of low volatility. The olefine oxide can be used as such or it can be subjected to certain subsequent purification steps in order to remove therefrom the possible traces of by-products, such as aldehydes.

Various types of apparatuses which are in themselves known can be used to carry out these separations. Thus, it is possible to use all types of distillation columns comprising all types of boilers, such as conventional boilers or film evaporators. These separations are generally carried out by distillation. The pressures and temperatures at which these separations are carried out can vary from one separation to the other and depend on the nature of the olefine, the volatile solvent and the olefine oxide. In general, in order to avoid secondary reactions (decomposition and the like) in the boilers of the distillation columns, it is preferred to use fairly low distillation pressures which are most frequently between 0.5 E+03 Pa and 5 E+05 Pa. Pressures of 1 E+03 Pa to 1.2 E+05 Pa are suitable.

The olefine oxides obtained according to the invention can be used, in particular, for the manufacture of resins.

Figure 2:
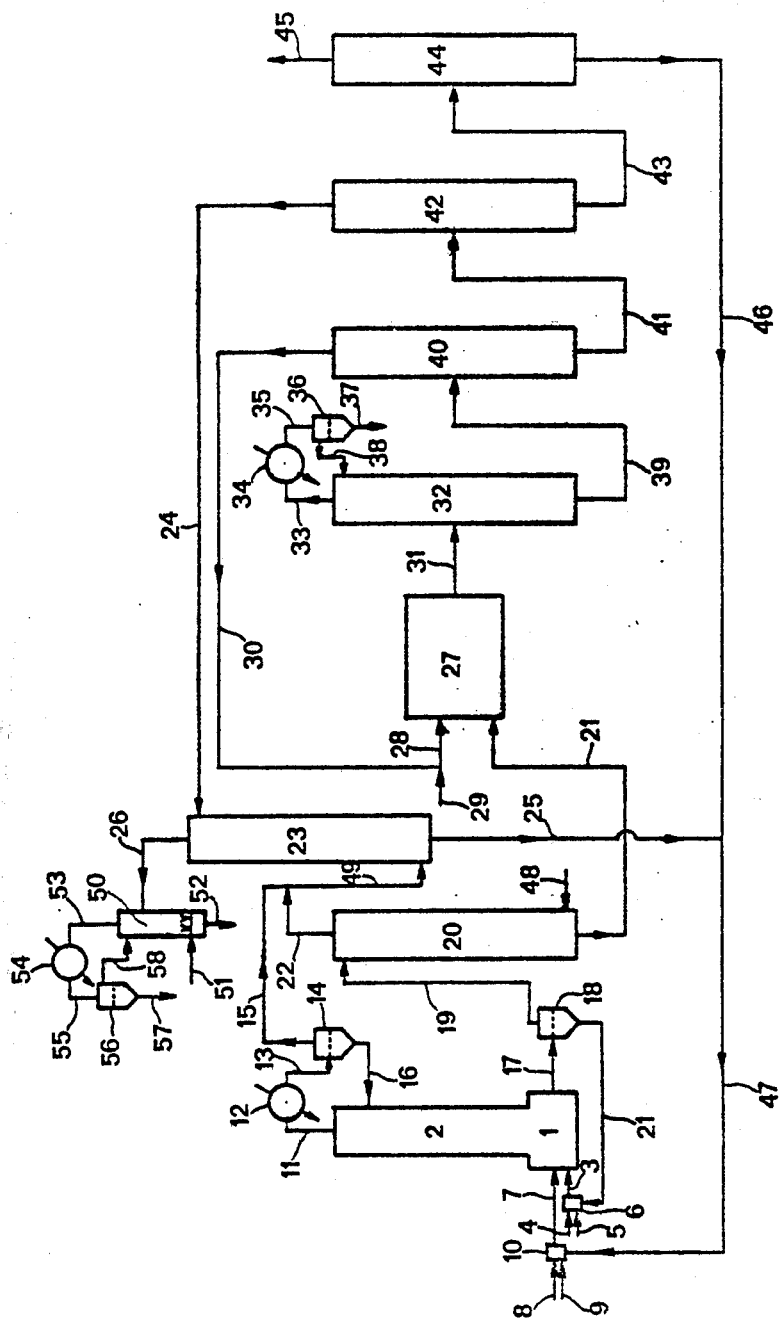
Figure 3:
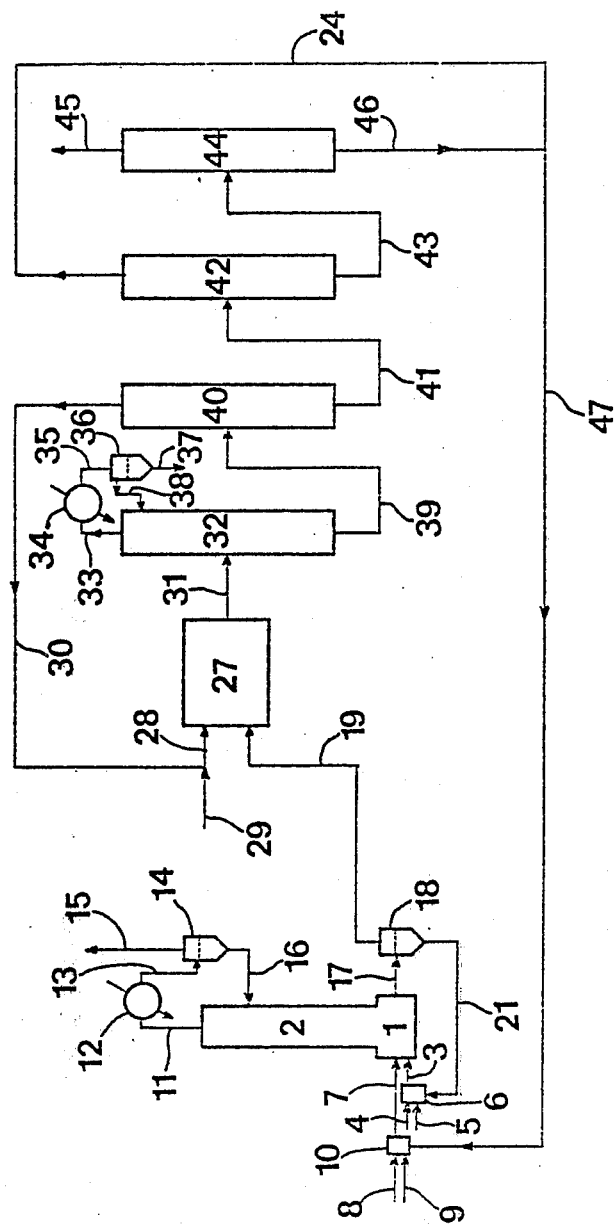

The process according to the invention can be carried out continuously in apparatuses such as those shown schematically in FIGS. 1, 2 and 3 of the attached drawings, which refer to particular practical embodiments.

According to the diagram shown in FIG. 1, the reactor 1 is surmounted by a distillation column 2; a concentrated solution of hydrogen peroxide and of catalyst, obtained by introducing fresh hydrogen peroxide and possibly a replenishing amount of catalyst via 4 and 5, respectively, into the mixer 6, is introduced into the reactor via 3. The mixer 6 is simultaneously fed via 21 with a recycled aqueous phase containing catalyst and a small amount of hydrogen peroxide. The fresh hydrogen peroxide can optionally be introduced in stages along this feed line (method not shown).

A solution of carboxylic acid in a mixture of volatile solvent and solvent of low volatility, which solution originates from the mixer 10, is simultaneously introduced into the reactor 1 via 7. The mixer 10 is fed via 47 with a recycled organic solution containing the carboxylic acid, the solvent of low volatility and the volatile solvent, it being possible for the latter to be introduced separately into the mixer (method not shown). Additions of fresh carboxylic acid via 8 and of fresh solvents via 9 are provided in order to compensate the losses in the installation and the purges.

During the reaction, the water/volatile solvent azeotrope leaves the distillation column 2 via 11, is condensed in the condenser 12 and is sent via 13 to the settling tank 14. If the volatile solvent has a greater density than water, the water is collected at the top of the settling tank via 15 and the volatile solvent is collected at the bottom of the settling tank via 16; in the opposite case, the withdrawals are reversed.

The volatile solvent is recycled via 16 to the distillation column 2, where it constitutes the reflux. In certain cases, part of this volatile solvent can be sent to the mixer 10, where it serves as solvent for the carboxylic acid (method not shown).

Part of the reaction mixture is continuously withdrawn from the mixer reactor via 17 and is sent to the settling tank 18. If the density of the organic phase is less than that of the aqueous phase, the organic phase, which contains the peracid, is withdrawn at the top of the settling tank 18 and is sent into the first washing zone 20 via 19. The aqueous phase is collected at the bottom of the settling tank 18 via 21 and is recycled to the mixer 6.

In the first washing zone 20, the organic phase introduced via 19 is subjected to washing in countercurrent with at least part of the water from the separation of the water/volatile solvent azeotrope by decantation, this water being introduced via 15bis and 60. A replenishing amount of fresh water can be provided via 59. Thus, a purified organic phase containing percarboxylic acid is collected via 21 and sent to the epoxidation reactor 27, and an aqueous solution containing hydrogen peroxide and possibly catalyst is collected via 22. The latter solution enters a second washing zone 23 via 22, this zone also being fed with recycled volatile solvent via 24. A solution containing hydrogen peroxide and volatile solvent is thus collected via 25 and it can either be recycled to the mixer 10 via 47 or it can be recycled to this same mixer directly (method not shown). The aqueous solution exhausted of hydrogen peroxide leaves the second washing zone 23 via 26.

The epoxidation reactor 27 is fed via 28 with olefine originating from recycling via 30 and with fresh olefine via 29.

The reaction mixture, which contains the olefine oxide in particular, leaves the reactor via 31 and enters a first distillation column 32, used for drying, at the top of which a water/volatile solvent or water/olefine azeotrope, depending on the particular case, is withdrawn via 33. The azeotrope is condensed at 34 and is sent via 35 to the settling tank 36. If the azeotrope is a water-/olefine azeotrope and if the density of water is greater than that of the olefine, the water is collected at the bottom via 37 and the olefine is collected at the top via 38. Depending on the densities of the liquids, the withdrawals can be reversed. The organic compound (olefine or volatile solvent, depending on the particular case) is recycled via 38 to the distillation column 32, where it constitutes the reflux.

The dry liquid mixture collected at the bottom of the column 32, which mixture contains the carboxylic acid, the olefine oxide, the volatile solvent, the solvent of low volatility and the unconverted reactants, is sent via 39 into the second distillation column 40, from which the olefine is drawn off at the top in the case where it has a lower boiling point than the volatile solvent. The olefine is recycled via 30 and 28 to the epoxidation reactor.

The first liquid product collected at the bottom of the column 40, which product contains the volatile solvent, the olefine oxide, the carboxylic acid and the solvent of low volatility, is sent via 41 into the third distillation column 42, from which the volatile solvent is withdrawn at the top and is recycled via 24 to the second washing zone 23. The second liquid product collected at the bottom of the column 42, which product contains the solvent of low volatility, the olefine oxide and the carboxylic acid, is sent via 43 into the fourth distillation column 44, from which the olefine oxide is withdrawn at the top via 45, and from which a solution of carboxylic acid in the solvent of low volatility is withdrawn at the bottom and is recycled via 46 and 47 to the mixer 10. The olefine oxide can be subjected to a subsequent distillation in order to remove therefrom the possible traces of impurities such as aldehydes and the like (method not shown). In the case where the volatile solvent has a lower boiling point than the olefine, the columns 40 and 42 are reversed. A certain number of purges are provided in the installation (method not shown).

The diagram shown in FIG. 2 is similar to that shown in FIG. 1, except as regards the two washing zones.

The organic phase, which contains the peracid and which is removed from the setting tank 18, is sent via 19 into the first washing zone 20, where it is subjected to washing in countercurrent with fresh water introduced via 48. Thus, a purified organic phase containing percarboxylic acid is collected via 21 and sent to the epoxidation reactor 27, and an aqueous solution containing hydrogen peroxide and possibly catalyst is collected via 22. This solution is sent, together with the water originating from the settling tank 14 via 15, into the second washing zone 23 via 49. The second washing zone is simultaneously fed with recycled volatile solvent via 24. A solution containing hydrogen peroxide and volatile solvent is thus collected via 25 and can be recycled via 47 to the mixer 10. The aqueous solution exhausted of hydrogen peroxide leaves the second washing zone 23 via 26 and is sent into the steam distillation column 50 in order to remove therefrom the small amounts of volatile solvent which could be dissolved therein. The steam distillation column 50 is fed with steam via 51. The water, which is free of volatile solvent but can contain small amounts of catalyst, is collected via 52. The vapours leaving the column 50 via 53 are condensed at 54 and sent via 55 to the settling tank 56. The volatile solvent separated off at 56 is collected at 57 and can be recycled to the peracidification (method not shown). The water separated off at 56 is returned via 58 to the column 50, where it provides the reflux.

The diagram illustrated in FIG. 3 is similar to those shown in FIGS. 1 and 2, except with regard to the washing zones.

The organic phase, which contains the peracid and which is withdrawn at the top of the settling tank 18 via 19, is sent into the epoxidation reactor 27, if appropriate after coalescence and additional separation by decantation. The aqueous phase collected at the top of the settling tank 14 via 15 is discarded. The volatile solvent, which is collected at the top of the distillation column 42, is returned via 24 and 47 to the mixer 10.

In order to illustrate the invention, without thereby limiting the scope thereof, an example of the manufacture of epichlorohydrin using perpropionic acid is given below (Example 1). Examples 2 and 3 demonstrate the favourable effect of 1,1,2,2-tetrachloroethane on the epoxidation rate.

EXAMPLE 1

The apparatus used is similar to that shown schematically in FIG. 1.

The process was applied to the manufacture of epichlorohydrin by epoxidising allyl chloride with perpropionic acid prepared from propionic acid.

The inert organic liquid used as the solvent contains 1,2-dichloropropane and 1,1,2,2-tetrachloroethane in a weight ratio of 13:52.

The reactor for the manufacture of the perpropionic acid is kept at a temperature of 330 K and under a pressure of 1.3 E+04 Pa.

A stirring system keeps the aqueous phase and the organic phase emulsified.

The two washing zones are kept at ambient temperature.

The epoxidation reactor consists of 5 mixer reactors arranged in a cascade, and is kept at a temperature of about 345 K under a pressure of about 1.01 E+05 Pa.

The composition of the product streams in the various zones of the installation (expressed in kg per hour) is given in Table 1 below. The selectivity of the epoxidation reaction with respect to the hydrogen peroxide employed is about 100%.

TABLE 1

| Constituents kg per hour | Line | | | | | | | |
|---|---|---|---|---|---|---|---|---|
| | 4 | 17 | 7 | 60 | 19 | 28 | 31 | 45 |
| propionic acid | | 0.474 | 0.538 | | 0.304 | | 0.509 | |
| perpropionic acid | | 0.423 | | | 0.252 | | | |
| water | 0.043 | 0.474 | | 0.072 | | | | |
| hydrogen peroxide | 0.101 | 0.049 | | | | | | |
| sulphuric acid | | 0.534 | | | | | | |
| 1,2-dichloropropane | | 0.157 | 0.157 | | 0.157 | | 0.157 | |
| 1,1,2,2-tetrachloroethane | | 0.628 | 0.628 | | 0.628 | | 0.628 | |
| allyl chloride | | | | | | 0.856 | 0.639 | |
| epichlorohydrin | | | | | | | 0.254 | 0.254 |
| various | | | | | | | 0.010 | |

EXAMPLES 2 and 3

Allyl chloride is reacted, at 313 K under atmospheric pressure, with a solution containing 162 g/kg of perpropionic acid in an organic solvent which is either 1,1,2,2-tetrachloroethane (Example 2) or 1,2-dichloropropane (Example 3).

The molar ratio of allyl chloride to perpropionic acid is equal to 2.

The solutions of perpropionic acid in the solvent also contain 41 g/kg of propionic acid.

It is found that the epoxidation rate of the allyl chloride in 1,1,2,2-tetrachloroethane (Example 2) is 1.7 times the rate measured in 1,2-dichloropropane.

What is claimed is:

1. In a process for the manufacture of an olefine oxide containing from 3 to 10 carbon atoms in its molecule and having a boiling point of at least 370° K. under atmospheric pressure by
   (1) reacting a carboxylic acid with hydrogen peroxide in a reactor in the presence of a catalyst and an inert organic solvent to yield a reaction mixture containing percarboxylic acid
   (2) withdrawing a portion of the reaction mixture containing percarboxylic acid from the reactor in step (1) and separating the withdrawn portion by decantation into an aqueous phase and an organic phase which comprises an organic solution of the percarboxylic acid in the organic solvent
   (3) epoxidizing olefine in an epoxidation reactor with the separated organic solution of percarboxylic acid obtained in step (2) to yield an epoxidation reaction mixture containing olefine oxide, the carboxylic acid, the inert organic solvent and unconverted olefine
   (4) separating from the mixture coming from the epoxidation step (3), olefine oxide and a carboxylic acid solution
   (5) recycling the separated carboxylic acid solution of step (4) to provide at least a portion of the carboxylic acid used in step (1), the improvement comprising:
   (6) employing as the inert organic solvent, a mixture of solvents which does not form an azeotrope with the olefine to be epoxidized or with the olefine oxide, and which comprises:
      (a) from 5 to 60% by weight of a volatile solvent, the boiling point of which is lower than the boiling point of the olefine oxide, and which forms with water a heterogeneous azeotrope and which serves to remove, by azeotropic distillation, the water in at least one of the reaction mixtures chosen from the reaction mixture containing percarboxylic acid in step (1) and the reaction mixture coming from the epoxidation reactor in step (3) and containing the olefine oxide,
   said volatile solvent being selected from the group consisting of solvents capable of forming, with water, a heterogeneous azeotrope with a minimum boiling point which is lower than the boiling point of other constituents and other possible azeotropes present in said reaction mixture, under equivalent pressure conditions,
      (b) a solvent of low volatility, the boiling point of which is higher than the boiling point of the olefine oxide and which serves as a solvent in the carboxylic acid solution recycled in step (5), and in case the solvent of low volatility is capable of forming an azeotrope with carboxylic acid, the boiling point of this azeotrope is higher than those of the olefine and olefine oxide, and
      (c) the solvents being not soluble in water and being not water solvents, the solvents being selected in a manner such that their mixture can dissolve at least 0.05 mol of carboxylic acid per liter, the solvent being selected from among carboxylic acid esters, ethers, halogenohydrocarbons, unsubstituted hydrocarbons, hydrocarbons substituted by nitro groups, nitric acid esters, and non-acid esters of carbonic and phosphoric acids,
   step (4) comprises separating from the reaction mixture coming from the epoxidation reactor of step (3), the unconverted olefine, the volatile solvent, the olefine oxide which constitutes the end product, and the solution of carboxylic acid, the solution of carboxylic comprising a solution containing the low-volatility solvent, by subjecting the reaction mixture coming from the epoxidation reactor of step (3) to several successive distillations during which
      (a) the uncoverted olefine is separated from a first liquid product containing the volatile solvent, the olefine oxide, the low volatility solvent and the carboxylic acid,
      (b) the first liquid product is separated into the volatile solvent and a second liquid containing the olefine oxide, the low volatility solvent and the carboxylic acid, and
      (c) the second liquid product is separated into the olefine oxide which constitutes the end product and the solution of carboxylic acid in the low volatility solvent
   (7) recycling the volatile solvent separated in step (4)(b) to the peracid fabrication reactor of step (1), and
   (8) removing, by azeotropic distillation with the volatile solvent, the water present in at least one of the mixtures selected from among the reaction mixture containing the percarboxylic acid of step (1) and the reaction mixture coming from the epoxidation reactor of step (3) and containing the olefine oxide.

2. Process according to claim 1, wherein the inert organic solvent contains from 5 to 35% by weight of the volatile solvent.

3. Process according to claim 1 or 2, wherein the volatile solvent is 1,2-dichloropropane.

4. Process according to claim 1 or 2, wherein the solvent of low volatility if 1,1,2,2-tetrachloroethane.

5. Process according to claim 1 or 2, wherein:
   step (1) further comprises removing water present in the reaction mixture by distilling the water/volatile solvent azeotrope, and maintaining a sufficient amount of water in the reaction mixture to allow the formation of an aqueous phase which is distinct from an organic phase containing the organic solvent and the percarboxylic acid;
   step (2) comprises separating the aqueous phase from the organic phase which constitutes the organic solution of percarboxylic acid in the organic solvent.

6. Process according to claim 5, wherein after separating off the aqueous phase in step (2), the organic solution of percarboxylic acid is washed with water so as to obtain a purified organic solution containing the percarboxylic acid, which is sent to the epoxidation, and an aqueous solution of hydrogen peroxide, and further comprising washing the aqueous solution of hydrogen peroxide with a part of the volatile solvent collected on separation of the epoxidation reaction mixture in a manner to obtain an aqueous solution exhausted of hydrogen peroxide and a solution of hydrogen peroxide in the volatile solvent, and recycling the obtained solution of hydrogen peroxide in the volatile solvent to step (1).

7. Process according to claim 6, wherein the washing with water is carried out using water collected after distillation and separation of the heterogeneous water/volatile solvent azeotrope.

8. Process according to claim 1 or 2, wherein the carboxylic acid is propionic acid.

9. Process according to claim 1 or 2, wherein the catalyst is sulphuric acid.

10. Process according to claim 1 or 2, comprising the epoxidation of allyl chloride to produce epichlorohydrin.

11. Process according to claim 1, wherein said volatile solvent is selected from the group consisting of 1,1-dichloropropane, 1,2-dichloropropane, cyclohexane, 1,2-dichloroethane, carbon tetrachloride, toluene and benzene.

12. Process according to claim 11, wherein said volatile solvent is 1,2-dichloropropane or 1,2-dichloroethane.

13. Process according to claim 1, wherein said solvent of low volatility is selected from the group consisting of 1,2,3-trichloropropane, tetrachloroethane, tetrachloroethylene, pentachloroethane, 1,4-dichlorobutane, meta-xylene, para-chlorotoluene, chlorobenzene, 1-nitropropane, nitrobenzene, methyl and ethyl chloroacetates, butyl acetate, diethyl carbonate, and tributyl phosphate.

14. Process according to claim 13, wherein said solvent of low volatility of 1,2,3-trichloropropane or 1,1,2,2-tetrachloroethane.

15. Process according to claim 1, wherein said olefine is selected from the group consisting of cyclohexane, butadiene, allyl alcohol, styrene and allyl chloride.

16. Process according to claim 1, wherein said inert organic solvent is a mixture of 1,2-dichloropropane and 1,1,2,2-tetrachloroethane.

17. In a process for the manufacture of an olefine oxide containing from three to ten carbon atoms in its molecule and having a boiling point of at least 370° K under atmospheric pressure by epoxidizing the corresponding olefine with an organic solution of a percarboxylic acid in an inert organic solvent, comprising:

(1) reacting the corresponding carboxylic acid with hydrogen peroxide in a reactor in the presence of a catalyst and an inert organic solvent to produce a reaction mixture containing the percarboxylic acid, the inert organic solvent comprising a mixture of solvents which does not form an azeotrope with the olefine to be epoxidized or with the olefine oxide, the mixture of solvents containing (a) from five to sixty percent of its weight of a volatile solvent whose boiling temperature is lower than the boiling temperature of the olefine oxide, the volatile solvent being one which forms with water a heterogeneous azeotrope and serves to remove, by azeotropic distillation, the water in at least one of the reaction mixtures chosen from the reaction mixture containing percarboxylic acid in step (1) and the reaction mixture coming from the epoxidation reactor of step (3) and containing the olefine oxide, said volatile solvent being selected from the group consisting of solvents capable of forming, with water, a heterogeneous azeotrope with a minimum boiling point which is lower than the boiling point of other constituents and other possible azeotropes present in the reaction mixture, from the manufacture of the percarboxylic acid, under equivalent pressure conditions;

(b) a low-volatility solvent whose boiling temperature is greater than the boiling temperature of the olefine oxide, and in case the solvent of low volatility is capable of forming an azeotrope with carboxylic acid, the boiling point of the azeotrope is higher than those of the olefine and olefine oxide; and (c) the solvents being not soluble in water and being not water solvents; the solvents being selected in a manner such that their mixture can dissolve at least 0.05 mole of carboxylic acid per liter; the solvents being selected from among the carboxylic acid esters, ethers, halogenohydrocarbons, non-substituted hydrocarbons, hydrocarbons substituted by nitro groups, nitric acid esters and non-acid esters of carbonic and phosphoric acids;

(2) withdrawing a portion of the reaction mixture containing percarboxylic acid from the reactor of step (1) and separating the withdrawn portion by decantation into an aqueous phase and an organic solution containing the percarboxylic acid in the inert organic solvent, (3) washing the separated organic solution of peracid of step (2) with water in a manner to obtain a purified organic solution containing the percarboxylic acid and an aqueous solution of hydrogen peroxide, (4) reacting the olefine with the purified organic solution of percarboxylic acid of step (3) in an epoxidation reactor to obtain an epoxidation reaction mixture containing olefine oxide, carboxylic acid, the inert organic solvent, and unconverted olefine, (5) separating from the epoxidation reaction mixture coming from the epoxidation reactor of step (4) the unconverted olefine, the volatile solvent, the olefine oxide which constitutes the end product, and a solution of carboxylic acid in the low-volatility solvent, by subjecting the reaction mixture coming from the epoxidation reactor of step (4) to several successive distillations during which (a) the unconverted olefine is separated from a first liquid product containing the volatile solvent, the olefine oxide, the low volatility solvent and the carboxylic acid, (b) the first liquid product is separated into the volatile solvent and a second liquid product containing the olefine oxide, the low volatility solvent and the carboxylic acid, and (c) the second liquid is separated into the olefine oxide which constituted the end product and a solution of carboxylic acid in the low volatility solvent (6) recycling the solution of carboxylic acid in the low-volatility solvent obtained in step (5) (c) to step (1), (7) washing the aqueous solution of hydrogen peroxide obtained in step (3) by means of at least part of the volatile solvent collected by the separation in step (5) of the epoxidation reaction mixture, the washing being conducted in a manner to obtain an aqueous solution exhausted of hydrogen peroxide and a solution of hydrogen peroxide in the volatile solvent, (8) recycling the solution of hydrogen peroxide in the volatile solvent obtained in step (7) to step (1), and (9) recycling the volatile solvent separated in step (5) (a) to the peracid fabrication reactor of step (1).

18. Process according to claim 1 or 2, wherein
said volatile solvent is selected from the group consisting of 1,1-dichloropropane, 1,2-dichloropropane, cyclohexane, 1,2-dichloroethane, carbon tetrachloride, toluene and benzene,
said solvent of low volatility is selected from the group consisting of 1,2,3-trichloropropane, tetrachloroethane, tetrachloroethylene, pentachloroethane, 1,4-dichlorobutane, meta-xylene, parachlorotoluene, chlorobenzene, 1-nitropropane, nitrobenzene, methyl and ethyl chloroacetates, butyl acetate, diethyl carbonate and tributyl phosphate, and
said olefine is selected from the group consisting of cyclohexane, butadiene, allyl alcohol, styrene and allyl chloride.

19. Process according to claim 1 or 2, wherein step (1) further comprises removing water present in the reaction mixture by distilling the water/volatile solvent azeotrope, and maintaining a sufficient amount of water in the reaction mixture to allow the formation of an aqueous phase which is distinct from an organic phase containing the organic solvent and the percarboxylic acid;
said volatile solvent is selected from the group consisting of 1,1-dichloropropane, 1,2-dichloropropane, cyclohexane, 1,2-dichloroethane, carbon tetrachloride, toluene and benzene;
said solvent of low volatility is selected from the group consisting of 1,2,3-trichloropropane, tetrachloroethane, tetrachloroethylene, pentachloroethane, 1,4-dichlorobutane, meta-xylene, parachlorotoluene, chlorobenzene, 1-nitropropane, nitrobenzene, methyl and ethyl chloroacetates, butyl acetate, diethyl carbonate, and tributyl phosphate; and
said olefine is selected from the group consisting of cyclohexane butadiene, allyl alcohol, styrene and allyl chloride.

20. Process according to claim 1, wherein water in the reaction mixture coming from the epoxidation reactor of step (3) is removed by the volatile solvent by azeotropic distillation.

* * * * *